United States Patent
Kwok

[19]

[11] Patent Number: 6,077,375

[45] Date of Patent: Jun. 20, 2000

[54] ELASTIC STRAND COATING PROCESS

[75] Inventor: Kui-Chiu Kwok, Mundelein, Ill.

[73] Assignee: Illinois Tool Works Inc., Glenview, Ill.

[21] Appl. No.: 09/060,581

[22] Filed: Apr. 15, 1998

[51] Int. Cl.[7] .............................. B32B 31/00; A61F 13/15
[52] U.S. Cl. ..................... 156/161; 156/229; 427/175; 427/207.1; 427/208.2; 427/208.4; 427/256; 427/422; 427/424; 427/427
[58] Field of Search ..................... 156/161, 163, 156/164, 229, 295; 427/175, 207.1, 208.2, 208.4, 210, 256, 422, 424, 427

[56] References Cited

U.S. PATENT DOCUMENTS

| | | |
|---|---|---|
| 1,868,690 | 7/1932 | Brigham . |
| 2,231,808 | 2/1941 | Isaac . |
| 2,424,743 | 2/1947 | Davis . |
| 3,459,615 | 8/1969 | Eilerman . |
| 3,543,332 | 12/1970 | Wagner et al. . |
| 3,615,995 | 10/1971 | Buntin . |
| 3,762,982 | 10/1973 | Whittington . |
| 4,098,632 | 7/1978 | Sprague, Jr. ............................. 156/295 |
| 4,147,580 | 4/1979 | Buell . |
| 4,259,220 | 3/1981 | Brunelle et al. . |
| 4,379,016 | 4/1983 | Stemmler et al. . |
| 4,418,123 | 11/1983 | Bunnelle et al. . |
| 4,473,986 | 10/1984 | Zeigler . |
| 4,525,229 | 6/1985 | Suzuki et al. . |
| 4,543,099 | 9/1985 | Brunelle et al. . |
| 4,626,305 | 12/1986 | Suzuki et al. . |
| 4,666,542 | 5/1987 | De Jonckheere . |
| 4,687,477 | 8/1987 | Suzuki et al. . |
| 4,710,187 | 12/1987 | Boland et al. . |
| 4,719,261 | 1/1988 | Bunnelle et al. . |
| 4,762,521 | 8/1988 | Roessler et al. . |
| 4,762,582 | 8/1988 | de Jonckheere . |
| 4,770,656 | 9/1988 | Proxmire et al. . |
| 4,788,089 | 11/1988 | Skipper . |
| 4,798,603 | 1/1989 | Meyer et al. . |
| 4,842,666 | 6/1989 | Werenicz ................................. 156/161 |
| 4,880,420 | 11/1989 | Pomparelli . |
| 4,891,249 | 1/1990 | McIntyre . |
| 4,900,384 | 2/1990 | Sanders et al. . |
| 4,917,696 | 4/1990 | De Jonckheere . |
| 4,949,668 | 8/1990 | Heindel et al. . |
| 4,982,688 | 1/1991 | Rothen . |
| 5,024,667 | 6/1991 | Malcom et al. . |
| 5,026,450 | 6/1991 | Cucuzza et al. . |
| 5,057,571 | 10/1991 | Malcom et al. . |
| 5,102,484 | 4/1992 | Allen et al. ......................... 156/244.11 |
| 5,208,064 | 5/1993 | Becker et al. .............................. 427/8 |
| 5,217,553 | 6/1993 | Marx et al. . |
| 5,275,676 | 1/1994 | Rooyakkers et al. ................... 156/164 |
| 5,507,909 | 4/1996 | Rollins et al. ........................... 156/425 |
| 5,525,175 | 6/1996 | Blenke et al. ........................... 156/161 |
| 5,577,306 | 11/1996 | Gold . |

FOREIGN PATENT DOCUMENTS

| | | |
|---|---|---|
| 0281857 | 2/1988 | European Pat. Off. . |
| 0322538 | 10/1988 | European Pat. Off. . |

*Primary Examiner*—Jeff H. Aftergut
*Attorney, Agent, or Firm*—Donald J. Breh

[57] ABSTRACT

A method for applying fluids to a strand and useable for bonding adhesive coated strands to substrates in the production of bodily fluid absorbing hygienic articles, by drawing the strand along an isolated path, moving a fluid or adhesive fiber back and forth across a path of the strand as the fluid fiber is dispensed toward the strand, and capturing substantially all of the fluid fiber on the isolated strand, and in some applications contacting an adhesive coated strand with the substrate to bond the strand thereto. The adhesive fiber is vacillated back and forth across a path of the strand beyond opposing sides thereof to at least partially coat all sides thereof with adhesive. In bodily fluid absorbing hygienic articles, the methods substantially eliminate fabric stiffening and loss of moisture absorbing capacity thereof, provide substantially uniformly bonding along the axial dimension of the strand to ensure uniform bunching of fabrics, optimum fluid absorption, and comfort.

24 Claims, 2 Drawing Sheets

ELASTIC STRAND COATING PROCESS

CROSS REFERENCE TO RELATED APPLICATIONS

The present application is related to U.S. application Ser. No. 08/843,224, filed Apr. 14, 1997, entitled "Improved Meltblowing Method and System", now U.S. Pat. No. 5,902,298 and to U.S. application Ser. No. 08/717,080, filed Oct. 8, 1996, entitled "Meltblowing Method and Apparatus", now U.S. Pat. No. 5,902,540 all commonly assigned and incorporated herein by reference.

BACKGROUND OF THE INVENTION

The invention relates generally to adhesive dispensing systems, and more particularly to processes for bonding one or more relatively elongated strands to one or more substrates, especially bonding stretched elastic strands to fabrics in the manufacture of bodily fluid absorbing hygienic articles.

It is often desirable to bond or adhere relatively elongated members, or strands, onto substrates. In the manufacture of a variety of bodily fluid absorbing hygienic articles including diapers, incontinence pads and other undergarments, for example, stretched elastic strands are bonded between fabrics to form waste bands and other stretchable portions thereof. In diapers, the waste bands and particularly the leg bands must provide relatively fluid tight seals between the undergarment and the body.

In known bodily fluid absorbing hygienic article manufacturing processes, adhesive is sprayed onto stretched elastic strands disposed on or very near an underlying fabric substrate moving relative to one or more adhesive dispensing nozzles. The adhesive is usually a hot melt adhesive dispensed in a swirling spiral pattern by a spiral nozzle, and is applied generously to both the substrate and the elastic strands simultaneously. The stretched elastic strand is usually bonded between overlapping fabric layers. As the stretched elastic strands contracts, the fabric adhered thereto is bunched together forming generally pleated waste bands and other stretchable portions of the undergarment. It is important that the elastic strand be bonded to the fabric substantially continuously along its axial length to ensure uniform pleating, or bunching, of the fabric, which is necessary for optimum comfort and fluid absorption, and to provide an aesthetically pleasing product.

U.S. Pat. No. 5,507,909, issued Apr. 16, 1996, entitled "Apparatus For The Manufacture Of An Elongated Element Comprising Helically Patterned Adhesive" discloses a process and apparatus for helically wrapping adhesive onto an elastic strand, which is bonded to a substrate in the manufacture of disposable absorbent products without coating adjacent areas of the substrate with large amounts of adhesive. To helically coat the elastic strand with adhesive, the strand is rotated about its axis as it is drawn past an adhesive flow from a dispensing orifice, for example by drawing the elastic strand between a nip roll assembly rotated at an angle relative thereto, or by other disclosed but less certain strand rotating means.

The known processes, however, generally apply much more adhesive onto the elastic strands and underlying substrate than is required for bonding, resulting in unnecessarily increased costs. The excess adhesive, which is usually hot, also has a tendency to deform the relatively thin, temperature sensitive fabric, thereby providing an undesirable appearance. In extreme cases the hot adhesive may destroy the fabric by burning a hole therethrough.

Another adverse effect of applying excessive amounts of adhesive onto fabrics is that the adhesive tends to stiffen the fabric. This stiffening is particularly undesirable in diaper and other undergarment applications where the elastic strand bunches the fabric to form waste bands and other stretchable portions that contact the body intimately. More particularly, the stiffened fabric tends not to bunch as freely and uniformly as it would otherwise, thereby compromising the ability of the fabric to form an effective fluid seal when stretched against the wearer's body.

The excess adhesive applied onto the fabric may also reduce the fluid absorbing capacity thereof, resulting possibly in the leakage of bodily fluids and in the accumulation of perspiratory moisture on the wearer's body, which may be particularly uncomfortable where waste and leg band portions of the garment contact the skin directly. Additionally, the adhesive stiffened fabric may be slightly abrasive against the skin, and in some extreme cases may irritate allergically sensitive skin.

The process and apparatus disclosed in the prior art U.S. Pat. No. 5,507,909 entitled "Apparatus For The Manufacture Of An Elongated Element Comprising Helically Patterned Adhesive" allegedly reduce the amount of adhesive applied to the substrate and apply more conservative amounts of adhesive onto the elastic strand, but the uniform application of adhesive helically about the strand requires consistently and uniformly controlling the rotation of the strand during the drawing thereof. It is questionable whether the elastic strand may be consistently rotated uniformly as required to uniformly apply adhesive helically thereabout in manufacturing operations. If the adhesive is not applied uniformly along the axial dimension of the strand, the stretched strand will not bond uniformly to the substrate, which adversely affects uniform bunching of the fabric. Non-uniform bunching is undesirable from an aesthetic viewpoint, and more substantively non-uniform bunching of the fabric compromises the ability of the fabric to form an effective fluid seal, and reduces the softness and comfort thereof when stretched against the wearer's body.

The present invention is drawn generally toward advancements in the art of applying fluids including adhesives onto strands, and more particularly toward bonding adhesive coated strands to substrates, especially adhesive coated elastic strands to fabrics in the manufacture of bodily fluid absorbing hygienic articles.

It is an object of the invention to provide novel methods for applying fluids to strands, and for bonding adhesive coated strands to substrates, and combinations thereof, that are economical and overcome problems in the prior art.

It is another object of the invention to provide novel methods for applying hot melt adhesives to elastic strands, and for bonding adhesive coated elastic strands to fabrics to form waist bands and other stretchable portions in the manufacture of a variety of bodily fluid absorbing hygienic articles and disposable absorbent products using reduced amounts of adhesive.

It is a further object of the invention to provide novel methods for bonding adhesive coated elastic stands to fabric substrates in the manufacture of a variety of bodily fluid absorbing hygienic articles, wherein the elastic strand is bonded to the fabric substantially uniformly along an axial length thereof to ensure uniform bunching of the fabric, thereby providing optimum comfort and fluid absorption, and an aesthetically pleasing, more marketable product.

It is yet another object of the invention to provide novel methods for reducing the amount of adhesive applied to elastic strands bonded to underlying fabric substrates in the manufacture of a variety of bodily fluid absorbing hygienic articles to reduce the possibility of melting the fabric with hot melt adhesives, to substantially eliminate fabric stiffening and to eliminate loss of moisture absorbing capacity thereof, and to reduce costs, especially costs associated with excess adhesive usage.

It is a more particular object of the invention to provide novel methods for applying fluids to a strand, useable for bonding the strand to a substrate in the production of bodily fluid absorbing hygienic articles, by drawing the strand along an isolated path, moving a fluid fiber across a path of the strand as the fluid fiber is dispensed toward the strand so that the fiber contacts the strand, and capturing substantially all of the fiber on the isolated strand. The fiber is preferably vacillated back and forth across a path of the strand, and beyond opposing sides thereof to at least partially coat all sides thereof with fluid.

It is another more particular object of the invention to provide novel methods for bonding strands to substrates in the production of bodily fluid absorbing hygienic articles by drawing the strand along a path separated spatially from the substrate, dispensing an adhesive fiber toward the strand so that at least a portion of the adhesive fiber crosses the path of the strand and contacts the strand, capturing substantially all of the adhesive fiber on the strand when the strand is spatially separated from the substrate to at least partially coat the strand with adhesive, and contacting the adhesive coated strand with the substrate to bond the strand thereto. The fiber is preferably vacillated back and forth across a path of the strand, and beyond opposing sides thereof to at least partially coat all sides thereof with adhesive.

These and other objects, aspects, features and advantages of the present invention will become more fully apparent upon careful consideration of the following Detailed Description of the Invention and the accompanying Drawings, which may be disproportionate for ease of understanding, wherein like structure and steps are referenced generally by corresponding numerals and indicators.

DETAILED DESCRIPTION OF THE INVENTION

Figure 1:
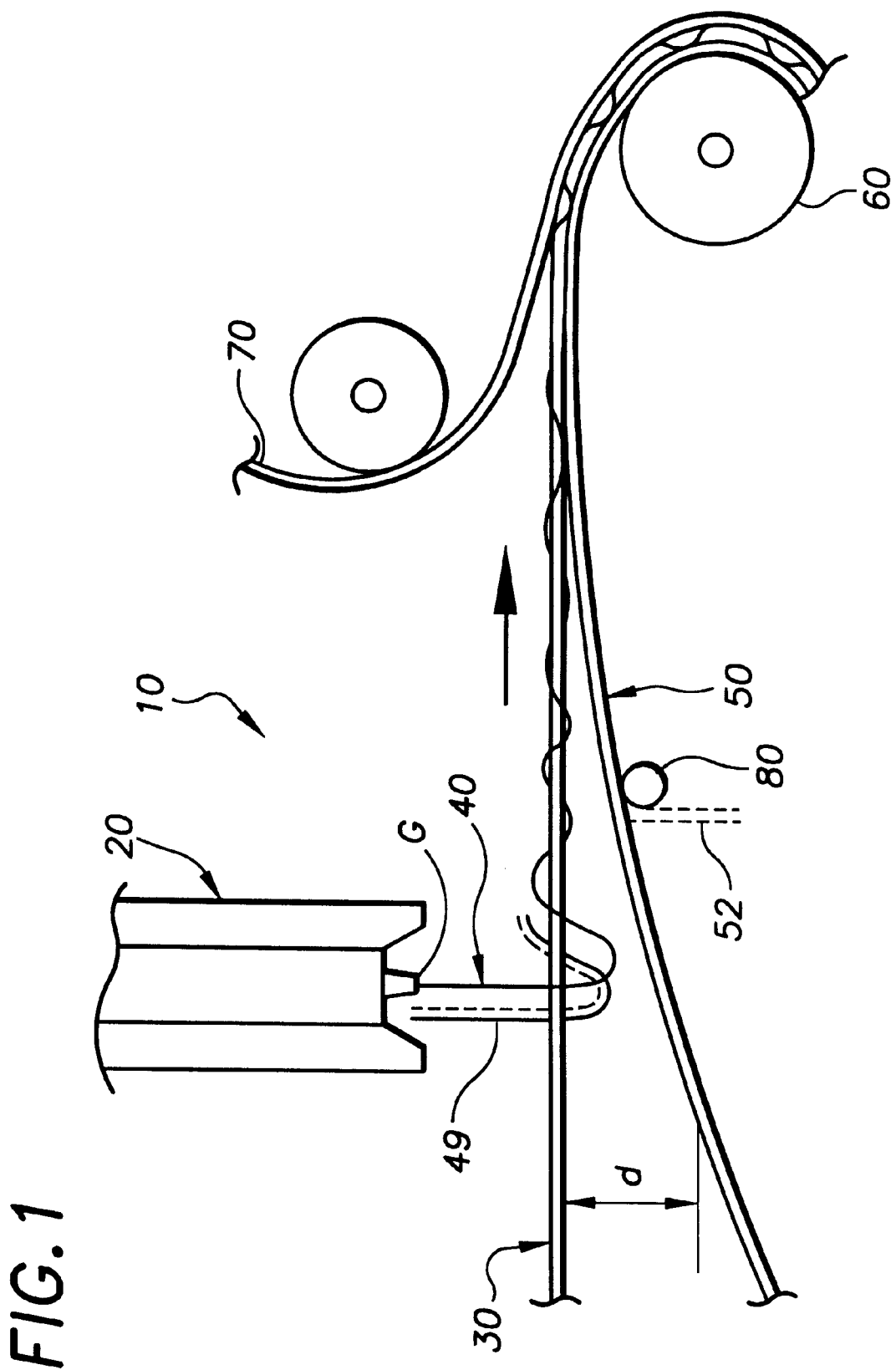
FIG. 1 is a partial side elevational view of a system for applying fluids to strands, and for bonding adhesive coated strands to substrates according to an exemplary embodiment of the invention.

FIG. 1 is a system 10 for practicing methods of applying fluids including adhesives to strands, and in some applications, bonding adhesive coated strands onto substrates according to the present invention. The exemplary system 10 dispenses hot melt adhesive fibers 40 from one or more adhesive dispensing nozzles 20, which are preferably meltblowing nozzles having one or more adhesive orifices and corresponding first and second air dispensing orifices disposed on opposing sides thereof as shown in FIG. 2 and discussed further below. The present invention is applicable more generally to applying fluids 40 to strands 30, which capture substantially all of the fluid dispensed from the nozzle 20 to prevent unwanted application of fluid onto an underlying substrate or other areas and to reduce fluid waste.

An exemplary application is the bonding of adhesive coated stretchable elastic strands 30 onto fabric substrates 50 in the manufacture of a variety of bodily fluid absorbing hygienic articles. The methods of the present invention are particularly useful in applications where it is desirable generally to precisely control the dispensing of relatively viscous fluids, including but not limited to hot melt adhesive fibers, onto a strand, and in some applications thereafter to bond adhesive coated strands onto substrates as discussed further below. Thus the fluid fibers 40 dispensed from the nozzle 20 are not necessarily limited to meltblown fibers, but are more generally any fluid that may be controllably dispensed so that substantially the entire fluid is captured by the strand 30.

In FIG. 1, the nozzle 20 dispenses a fluid fiber 40 toward an isolated strand 30 drawn along a path so that at least a portion of the fluid fiber 40 crosses the path of the strand 30 and contacts the strand so that the fluid fiber 40 attaches thereto. The spatially isolated strand 30 captures substantially all of the fiber fluid 40 dispensed from the nozzle 20, whereby the strand 30 is at least partially coated with fluid. By capturing substantially all of the fluid dispensed from the nozzle 20 onto the spatially isolated strand 30 there is little or no wasted fluid, thereby economizing the application thereof. Capturing all of the fluid fiber 40 onto the strand 30 also reduces the likelihood that fluid will spill-over or be applied inadvertently to unintended areas, for example underlying substrates.

Figure 2A:
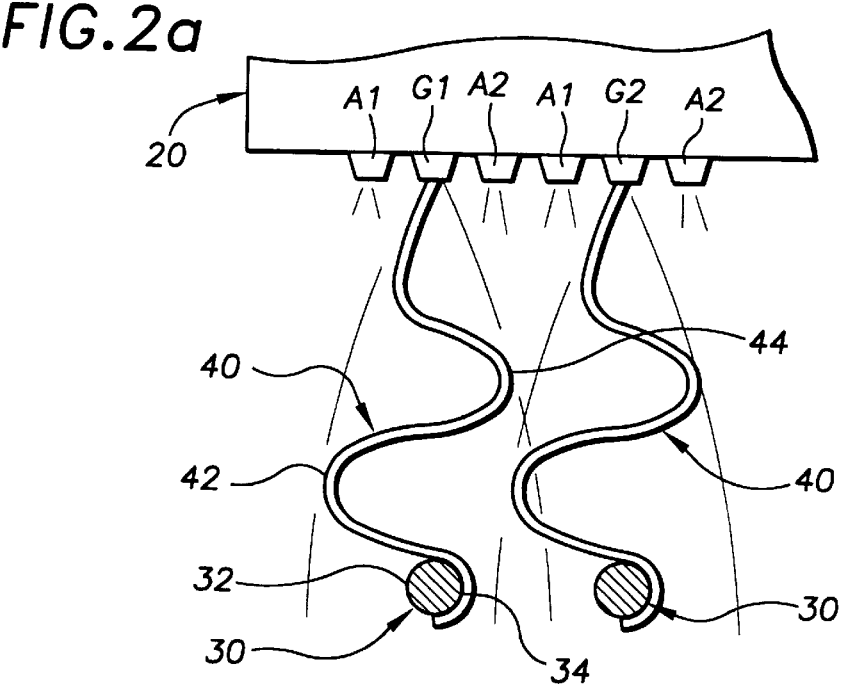
FIG. 2a is a partial sectional view of fluid fibers dispensed toward corresponding strands.
Figure 2B:
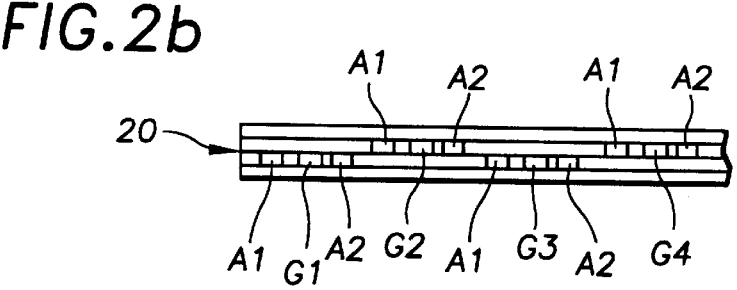
FIG. 2b is an end view of an exemplary nozzle for dispensing a plurality of fluid fibers toward a corresponding plurality of strands.

The fluid fiber 40 is preferably a substantially continuous fiber, although it may be intermittently discontinuous so long as a portion of the fiber crosses the path of the strand and attaches thereto. FIG. 2a illustrates the fluid fiber preferably moving back and forth across the path of the strand 30 as the fluid fiber 40 is dispensed toward the strand 30. The viscosity, mass, and range of movement of the fluid fiber 40 back and forth across the path of the strand 30 are selected or controlled so that the spatially isolated strand 30 captures substantially all of the fluid fiber 40 dispensed from the nozzle 20. Variations in the dispensing of the fluid fiber 40 from the nozzle 20, resulting for example from supply pressure changes and residue accumulation in the nozzle orifice and other factors, may result in fluid fiber 40 discontinuities or in fluid dispensing irregularities that occasionally prevent the fibers 40 or portions thereof from being captured entirely by the strand 30.

Figure 3:
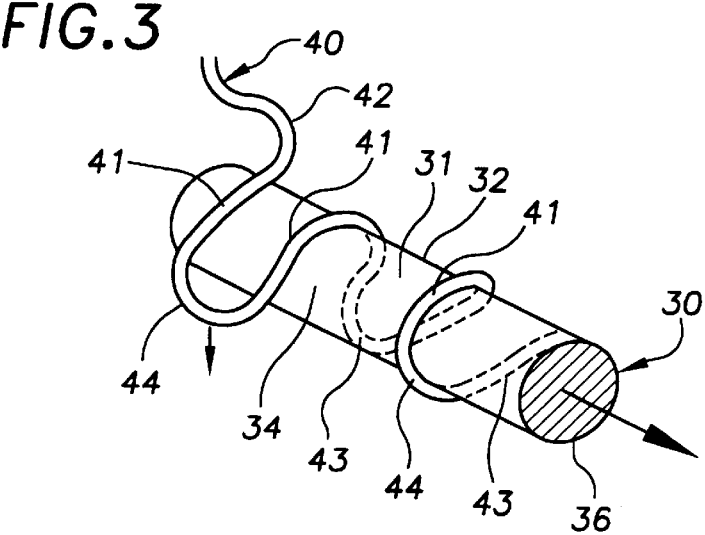
FIG. 3 is a partial perspective view of a strand at least partially coated with fluid on all sides thereof according to an exemplary embodiment of the invention.

FIGS. 2a and 3 illustrate the fluid fiber 40 moving back and forth across a path of the strand 30, wherein fluid fiber portions 42 and 44 move beyond corresponding opposing sides 32 and 34 of the strand 30 as the fluid fiber 40 is dispensed toward the strand 30. Fluid fibers thus dispensed are captured substantially entirely by the strand 30, whereby all sides of the strand 30 are at least partially coated with fluid. Thus applied, the adhesive fibers 40 coat the strand 30 substantially uniformly along the axial dimension or length thereof, which is desirable in many applications, particularly in the manufacture of bodily fluid absorbing hygienic articles where it is desirable to uniformly bond an adhesive coated elastic strand onto a fabric substrate to uniformly bunch the fabric forming waste bands and other stretchable portions thereof. Substantially uniformly applying the adhesive fibers 40 along the axial dimension of the strand 30 without coating the entire strand also substantially reduces adhesive usage while providing relatively uniform bonding to the substrate.

FIG. 3 illustrates, more particularly, the fiber portions 42 and 44 draping downwardly along the corresponding sides 32 and 34 of the strand 30 after other fiber portions 41 contact the strand 30. The fiber portions 42 and 44 are preferably dispensed by the nozzle 20 to extend sufficiently outwardly beyond the corresponding sides 32 and 34 of the strand 30 so that portions thereof 43 adhere also to an underside 36 of the strand 30. In some applications, the fiber portions 42 and 44 may even extend and adhere down along one side of the strand, across the underside thereof, and back upwardly along the opposing side of the strand 30, sometimes wrapping more than once about the strand.

The portions 42 and 44 of the fiber moving back and forth across the path of the strand 30 drape over the strand 30 under the influence of momentum or gravity or a combination thereof, and ultimately the fiber 40 adheres at least partially to all sides of the strand 30 including a top side 31, opposing sides 32 and 34, and the underside 36 thereof. The adhesive fiber 40 is dispensed preferably from the nozzle 20 located above the isolated strand 30, and adheres initially to the top side 31 of the strand 30. The fiber 40 then migrates downwardly along the sides of the strand 30 and across the underside thereof to at least partially coat all sides thereof. The adhesive may thus be applied uniformly along the axial dimension of the strand 30, without coating the entire strand, thereby economizing on the application of adhesive and at the same time applying adequate amounts thereof to the strand to ensure uniform bonding of the strand 30 along the axial dimension thereof to the substrate.

The fiber portions 42 and 44 preferably are not dispensed to extend so far outwardly beyond the corresponding sides 32 and 34 of the strand 30 that the fluid fiber 40 can not be captured substantially entirely by the strand 30. The fluid fiber mass flow rate, fluid viscosity, and size and stability of the strand 30 are among the factors that limit the extent to which the fiber 40 may extend beyond the sides of the strand 30 and ultimately be substantially entirely captured thereby.

Precisely controlling the dispensing of fluid fibers from the nozzle 20 ensures that the strand 30 captures substantially all of the fluid fiber 40. Precisely controlling the dispensing of the fluid fibers 40 also ensures that fluid is applied at least partially to substantially all sides of the strand 30 and substantially uniformly along the axial dimension thereof. By appropriately controlling the dispensing of the fluid, and generally the rate at which the strand 30 is drawn relative to the nozzle 20, it is possibly to accurately control the amount or quantity of fluid applied to the strand.

In the exemplary application, the fluid fiber 40 is a substantially continuous hot melt adhesive fiber dispensed from an adhesive orifice G of a meltblowing nozzle 20. FIG. 2a illustrates the adhesive fiber 40 vacillating back and forth across the path of the strand 30 and beyond opposing sides thereof under the influence of first and second air flows dispensed from first and second air orifices A1 and A2 disposed on opposing sides of corresponding adhesive orifices G1 and G2 of the nozzle 20. The amplitude and frequency of vacillation of adhesive fibers 40 is controlled by the first and second air flows as disclosed more fully in the referenced copending U.S. application Ser. No. 08/843,224, entitled "Improved Meltblowing Method and System", and copending U.S. application Ser. No. 08/717,080, entitled "Meltblowing Method and Apparatus". In an alternative embodiment, hot melt adhesive fibers are dispensed from a spiral nozzle in a swirling pattern to move the adhesive fiber back and forth across the path of the strand as the adhesive fiber is dispensed toward the strand. The meltblowing nozzles of the types disclosed in the referenced copending U.S. application Ser. No. 08/843,224, entitled "Improved Meltblowing Method and System", and copending U.S. application Ser. No. 08/717,080, entitled "Meltblowing Method and Apparatus", however are believed to provide relatively superior control over the adhesive flow in comparison to known spiral nozzles, and are particularly suitable for applying adhesive fibers, which are capturable substantially entirely by corresponding strands according to the present invention.

In applications where the strand 30 is bonded between substrates and where the strand 30 has a tendency to twist prior to bonding onto a single substrate, it is desirable to at least partially coat all sides of the strand 30 with adhesive, to ensure complete bonding of the strand 30 to the substrate 50. It is desirable in other applications, for example where an elastic strand 30 forms a waste band or other stretchable portion of a garment, to apply adhesive substantially uniformly along the axial dimension thereof, and preferably at least partially to all sides of the strand, to ensure uniform bonding of the strand 30 along an axial dimension thereof to a fabric substrate, thereby providing substantially uniform bunching of the fabric as the elastic strand contracts. The extent to which the strand 30 is coated with adhesive is controlled generally by the adhesive fiber mass flow rate, fiber vacillation amplitude and frequency, and the strand drawing rate.

FIG. 1 illustrates the application of adhesive fibers onto a strand 30 and bonding of the adhesive coated strand 30 to a substrate 50. Initially, the strand 30 is drawn along a path separated spatially from the substrate 50. The adhesive fiber 40 is dispensed toward the isolated strand 30 so that at least a portion of the adhesive fiber 40 crosses the path of the strand 30 and attaches thereto, as shown in FIG. 2. As discussed above, the fiber 40 is preferably vacillated back and forth across the path of the strand 30, beyond opposing sides thereof. The strand 30 captures substantially all of the adhesive fiber 40 when the strand 30 is spatially separated from the substrate 50 to at least partially coat the strand 30 with adhesive. Preferably, the adhesive is applied at least partially to all sides of the strand 30 to ensure uniform bonding of the strand along an axial dimension thereof to the substrate 50. The adhesive coated strand 30 is then contacted with the substrate 50 to bond the strand 30 thereto before the adhesive sets.

In the manufacture of bodily fluid absorbing hygienic articles, the substrate 50 is fabric, and the strand 30 is an elastic strand that is stretched by applying tension thereto before bonding to the substrate 50. FIG. 1 illustrates the strand 30 and the substrate 50 both drawn by common roller 60. In this exemplary application, the stretched adhesive coated elastic strand 30 is also bonded to a second fabric substrate 70, which may also be drawn by the roller 60, whereby the strand 30 is disposed between and bonded to the substrate 50 and the substrate 70. The adhesive is applied at least partially to all sides of the strand 30 and preferably substantially uniformly along the axial dimension thereof as discussed above to ensure that the strand 30 bonds uniformly to both fabric substrates 50 and 70.

In applications where the substrate 50 is adjacent the strand 30 and opposite the adhesive dispensing nozzle 20, it is necessary to spatially separate the substrate 50 from the strand 30 by a distance "d" greater than a droop distance of the adhesive fiber 40 below the strand 30 opposite the adhesive nozzle 20 to prevent adhesive from inadvertently adhering to the substrate 50. In other applications, the adhesive 40 may be applied to the strand 30 away from the substrate 50, to ensure that no adhesive 40 is inadvertently applied thereto, wherein the substrate 50 may be supplied for example from below roller 80 along the path 52 away from fluid fibers 40 dispensed from the nozzle 20.

FIG. 2a illustrates the nozzle 20 dispensing a plurality of at least two fluid or adhesive fibers 40 from a corresponding plurality of adhesive orifices G1 and G2 toward corresponding isolated strands 30, wherein each of the plurality of adhesive fibers 40 is vacillated back and forth across the path of the corresponding strand 30 with a plurality of corresponding first and second air flows dispensed from first and second air orifices A1 and A2 disposed on opposing sides of the corresponding adhesive orifices G1 and G2, according to the modes of operation discussed above, and particularly those disclosed more fully in the referenced copending U.S. application Ser. No. 08/843,224, entitled "Improved Meltblowing Method and System", and copending U.S. application Ser. No. 08/717,080, entitled "Meltblowing Method and Apparatus".

Each strand 30 captures substantially all of the adhesive fiber 40 dispensed from the corresponding adhesive orifice G1 and G2 when the strand 30 is spatially separated from the substrate to at least partially coat the strand 30 with adhesive. The adhesive fibers are preferably vacillated back and forth across the path of the corresponding strand beyond opposing sides thereof to at least partially coat all sides of each strand with adhesive, preferably substantially uniformly along the axial dimension thereof. In some applications, the plurality of adhesive coated strands are subsequently contacted with one or more substrates to bond the plurality of strands thereto as discussed above.

FIG. 2a illustrates the plurality of adhesive orifices G1 and G2 and corresponding air orifices of the nozzle 20 arranged generally in a series. In one embodiment illustrated in FIG. 2b, adjacent adhesive fibers are dispensed from adhesive orifices G1 and G2 with corresponding air orifices A1 and A2 disposed, or offset, relative to each other in different planes of the nozzle 20. For example, all odd numbered adhesive orifices G1 and G3 and the corresponding air orifices are disposed serially in a first plane, and all even numbered adhesive orifices G2 and G4 and the corresponding air orifices are disposed serially in a second plane different from the first plane, whereby adjacent adhesive flows are offset axially along the strand 30, as illustrated by adhesive flows 40 and 49 in FIG. 1. Alternatively, all of the adhesive dispensing orifices may be disposed in series in a single common plane. These various aspects of the adhesive dispensing nozzles are disclosed more fully in the referenced copending U.S. application Ser. No. 08/843,224, entitled "Improved Meltblowing Method and System", and copending U.S. application Ser. No. 08/717,080, entitled "Meltblowing Method and Apparatus".

FIG. 2a illustrates the amplitude of vacillation of adjacent fibers 40 apparently overlapping without interference therebetween. More particularly, when the adhesive dispensing orifices G1 ad G2 are adjacent to each other in a common plane, the vacillating fibers 40 dispensed therefrom have a tendency to synchronize or to deflect from the common plane one way or the other along an axial direction of the corresponding strand 30 to avoid interference with each other. This phenomenon permits dispensing fluid or adhesive fibers 40 from relatively closely space adhesive dispensing orifices toward relatively closely spaced corresponding strands 30, wherein the adhesive fibers 40 vacillate apparently overlappingly but without interference therebetween. The vacillating fibers 40 are thus captured substantially entirely by the corresponding strands 30, as discussed above, without interference from adjacent fibers 40 and without spillage or overspray of adhesive resulting from interference between or entanglement of the adjacent fibers.

While the foregoing written description of the invention enables one of ordinary skill to make and use what is considered presently to be the best mode thereof, those of ordinary skill will appreciate and acknowledge the existence of variations, combinations, and equivalents of the specific exemplary embodiments herein. The invention is therefore to be limited not by the exemplary embodiments, but by all embodiments within the scope and spirit of the appended claims.

What is claimed is:

1. A method for applying a fiberized fluid to a strand, the method comprising:

drawing a strand along an isolated path;

dispensing a substantially continuous fluid fiber toward the strand;

vacillating the continuous fluid fiber back and forth across the path of the strand, non-parallel to the path of the strand as the fluid fiber is dispensed toward the strand;

capturing substantially all of the continuous fluid fiber on the strand; and coating all sides of the strand at least partially with the fluid fiber.

2. The method of claim 1, vacillating the fluid fiber predominantly transversely to the path of the strand and beyond opposing sides of the strand as the fluid fiber is dispensed toward the strand, wrapping portions of the fluid fiber about the strand.

3. The method of claim 1, the fiberized fluid is an adhesive fiber, the method further comprising:

drawing the strand along a path separated spatially from a substrate;

dispensing the adhesive fiber from above the strand;

vacillating the adhesive fiber predominantly non-parallel to the path of the strand;

capturing substantially all of the adhesive fiber on the strand along the axis thereof when the strand is spatially separated from the substrate;

coating all sides of the strand at least partially with the adhesive fiber when the strand is spatially separated from the substrate; and contacting the adhesive coated strand with the substrate to bond the strand to the substrate.

4. The method of claim 3, the strand is an elastic strand and the substrate is a fabric for a bodily fluid absorbing hygienic article, the method further comprising stretching the elastic strand before bonding the elastic strand to the substrate.

5. The method of claim 3 further comprising spatially separating the strand from the substrate by a distance greater than a droop distance of the adhesive fiber below the strand opposite from where the adhesive fiber is dispensed from above the strand.

6. The method of claim 3 the adhesive fiber is a hot melt adhesive, the method further comprising dispensing the adhesive fiber from a spiral nozzle in a swirling pattern to move the adhesive fiber back and forth across the path of the strand beyond opposing sides of the strand as the adhesive fiber is dispensed toward the strand.

7. The method of claim 3 further comprising bonding the adhesive coated strand to a second substrate, whereby the strand is disposed between the substrate and the second substrate.

8. The method of claim 3, dispensing the adhesive fiber from an adhesive orifice of a meltblowing nozzle, vacillating the adhesive fiber predominantly transversely to the path of the strand and beyond opposing sides of the strand with exactly two air flows dispensed from first and second air orifices disposed on substantially opposing sides of the adhesive orifice.

9. The method of claim 8 further comprising controlling the amplitude and frequency of vacillation of the adhesive fiber with the exactly two air flows so that substantially all of the adhesive fiber is captured by the strand.

10. The method of claim 3, substantially uniformly coating the strand with the adhesive fiber along an axial dimension of the strand.

11. The method of claim 3 further comprising:

drawing a plurality of at least two strands separated spatially from the substrate;

dispensing a plurality of adhesive fibers from a corresponding plurality of adhesive orifices of a meltblowing nozzle toward a corresponding one of the plurality of strands;

vacillating each of the plurality of adhesive fibers back and forth across the path of the corresponding strand, predominantly non-parallel to the path of the corresponding strand and beyond opposing sides of the corresponding strand with exactly two air flows dispensed from first and second air orifices disposed on substantially opposing sides of the corresponding adhesive orifice;

capturing substantially all of each adhesive fiber on the corresponding strand when the strand is spatially separated from the substrate;

at least partially coating all sides of each strand with the corresponding adhesive fiber when the strand is spatially separated from the substrate; and contacting the plurality of adhesive coated strands with the substrate to bond the plurality of strands to the substrate.

12. The method of claim 11 further comprising dispensing the air flows from the corresponding air orifices arranged in series with the corresponding plurality of adhesive orifices.

13. The method of claim 11 further comprising dispensing at least two adjacent adhesive fibers from corresponding adhesive orifices offset axially relative to each other along the path of the strand.

14. A method for applying adhesive to a strand, useable for bonding the strand to a substrate in the production of bodily fluid absorbing hygienic articles, the method comprising:

drawing a strand along a path separated spatially from the substrate;

dispensing a substantially continuous adhesive fiber toward the strand;

vacillating the continuous adhesive fiber back and forth across the path of the strand, non-parallel to the path of the strand as the adhesive fiber is dispensed toward the strand;

capturing substantially all of the continuous adhesive fiber on the strand when the strand is spatially separated from the substrate; and contacting the adhesive coated strand with the substrate to bond the strand to the substrate.

15. The method of claim 14, vacillating the adhesive fiber predominantly transversely to the path of the strand and beyond opposing sides of the strand as the adhesive fiber is dispensed toward the strand, wrapping portions of the adhesive fiber about the strand.

16. The method of claim 14, the strand is an elastic strand and the substrate is a fabric for a bodily fluid absorbing hygienic article, the method further comprising stretching the elastic strand before the elastic strand is bonded to the substrate.

17. The method of claim 14, dispensing the adhesive fiber from an adhesive orifice of a meltblowing nozzle, vacillating the adhesive fiber predominantly between exactly two air flows dispensed from first and second air orifices disposed on substantially opposing sides of the adhesive orifice.

18. The method of claim 14 further comprising vacillating the adhesive fiber predominantly between exactly two air flows on substantially opposing sides of the adhesive fiber.

19. The method of claim 18 further comprising controlling the amplitude and frequency of vacillation of the adhesive fiber with the exactly two air flows so that the strand is coated substantially uniformly with the adhesive fiber along an axial dimension of the strand.

20. The method of claim 14 further comprising dispensing the adhesive fiber from above the strand, and spatially separating the strand from the substrate by a distance greater than a droop distance of the adhesive fiber below the strand opposite from where the adhesive fiber is dispensed from above the strand.

21. The method of claim 17 further comprising:

drawing a plurality of at least two strands along corresponding paths separated spatially from the substrate;

dispensing a plurality of substantially continuous adhesive fibers from a corresponding plurality of adhesive orifices of the nozzle toward a corresponding one of the plurality of strands;

vacillating each of the plurality of adhesive fibers back and forth across the path of the corresponding strand, non-parallel to the path of the corresponding strand predominantly between exactly two air flows dispensed from corresponding air orifices disposed on substantially opposing sides of the corresponding adhesive orifice;

capturing substantially all of each adhesive fiber on the corresponding strand when the strand is spatially separated from the substrate; and contacting the plurality of adhesive coated strands with the substrate to bond the plurality of strands to the substrate.

22. The method of claim 21 further comprising dispensing the air flows from the corresponding air orifices arranged in series with the corresponding plurality of adhesive orifices.

23. The method of claim 21 further comprising dispensing at least two adjacent adhesive fibers from corresponding adhesive orifices offset axially relative to each other along the path of the strand.

24. The method of claim 14, the adhesive fiber is a hot melt adhesive, the method further comprising dispensing the adhesive fiber from a spiral nozzle in a swirling pattern to move the adhesive fiber back and forth across the path of the strand as the adhesive fiber is dispensed toward the strand.

* * * * *

Adverse Decision In Interference

Patent No. 6,077,375, Kui-Chiu Kwok, ELASTIC STRAND COATING PROCESS, Interference No. 104,782, final judgment adverse to the patentee rendered October 18, 2002, as to claims 1-24.
*(Official Gazette November 26, 2002)*